United States Patent
Noïk et al.

(10) Patent No.: US 6,853,199 B2
(45) Date of Patent: Feb. 8, 2005

(54) INTERFACE DETECTOR

(75) Inventors: Christine Noïk, Le Pecq (FR); Michel Constant, Saint Denis (FR)

(73) Assignee: Institut Francais du Petrole, Rueil Malmaison Cedex (FR)

( * ) Notice: Subject to any disclaimer, the term of this patent is extended or adjusted under 35 U.S.C. 154(b) by 81 days.

(21) Appl. No.: 10/313,024

(22) Filed: Dec. 6, 2002

(65) Prior Publication Data

US 2003/0117150 A1 Jun. 26, 2003

(30) Foreign Application Priority Data

Dec. 13, 2001 (FR) .............................. 01 16096

(51) Int. Cl.$^7$ .................. G01R 27/08; G01R 27/04
(52) U.S. Cl. .................. 324/637; 324/644; 324/697
(58) Field of Search ............................. 324/639, 640, 324/637, 641, 335, 347, 697; 73/61.44, 861.04, 861.08, 861.11, 861.15

(56) References Cited

U.S. PATENT DOCUMENTS

| | | | | | |
|---|---|---|---|---|---|
| 4,947,127 | A | * | 8/1990 | Helms et al. | 324/640 |
| 5,101,163 | A | * | 3/1992 | Agar | 324/639 |
| 5,150,061 | A | * | 9/1992 | Castel et al. | 324/640 |
| 5,793,216 | A | * | 8/1998 | Constant | 324/639 |
| 6,332,087 | B1 | * | 12/2001 | Svenson et al. | 600/407 |
| 6,480,141 | B1 | * | 11/2002 | Toth et al. | 342/22 |

* cited by examiner

*Primary Examiner*—Anjan K. Deb
(74) *Attorney, Agent, or Firm*—Antonelli, Terry, Stout & Kraus, LLP

(57) ABSTRACT

A separating drum 1 is provided with a device for determining the position, the composition and the nature of several layers of fluid settling upstream from barrier 8. The device comprises a first rod 12 provided with microwave beam emitters 13, a second rod 14 provided with microwave beam receivers 15, a microwave source 16 that can be connected to emitters 13, and means 17 for recording and analyzing the microwave beams received by receivers 15.

12 Claims, 1 Drawing Sheet

INTERFACE DETECTOR

BACKGROUND OF THE INVENTION

1. Field of the Invention

The present invention relates to a device and to a method for determining the position of the interfaces between different fluids contained in a drum, as well as the nature and the composition of the fluids. In particular, the present invention applies to a petroleum effluent contained in a separating drum for determining the position of the gas/oil and oil/water interfaces, and for characterizing the emulsion located between the oil and the water and the foam located between the oil and the gas.

2. Description of the Prior Art

In petroleum production, the effluent produced consists of several fluids: oil (mixture of hydrocarbons), salt water and gas, and often solid particles, sand for example. Separation of the different fluids is carried out in a separating drum according to the density of each fluid. In the drum, separation is physically carried out by means of a barrier allowing the lightest fluid (oil) to flow and the heaviest fluid (water) to be blocked. The position and above all the geometry (height of the barrier) determine the efficiency of the separating drum. This physical barrier is defined during the design of the separating drum and it cannot be modified during production. It is consequently important to be able to control the incoming volume of water and oil and the respective oil and water levels.

Mixtures of oil and water separate spontaneously by settling linked with the density difference. However, for most systems, formation of an intermediate layer of emulsified nature occurs. Formation of an emulsion is difficult to predict and to control. It depends on the operating conditions such as stirring, the presence of a pump, of valves, and on parameters such as the pressure, the temperature and the physico-chemical composition of the oil and of the water. It is important to locate this emulsion layer and to know its volume during the separation stage so as to adjust the production flow rate to minimize the loss of water in oil and, conversely, the loss of oil in water. Furthermore, knowing the nature of the emulsion allows introduction of suitable demulsifying chemical agents upstream from the drum, or to activate flow stabilization devices in the separating drum.

WO-00/22,387 provides a separating drum equipped with gamma-ray detectors allowing notably to determine the position of the oil/water and gas/oil interfaces, and the thickness of the emulsion.

However, because of their radioactive nature, gamma-ray detectors can be dangerous and are difficult and delicate to handle. Gamma ray detectors do not allow determination of the nature of the emulsion. Besides, the use of radioactive sources poses approval problems.

SUMMARY OF THE INVENTION

The present invention provides a separating drum equipped with microwave beam emitters and receivers.

In general terms, the invention relates to a device for determining the position, the composition and the nature of several superposed fluid layers, comprising:

a separating drum containing at least two fluids arranged in superposed layers, the interface formed by the boundary between two layers being a horizontal plane, the drum comprising at least two microwave beam emitters arranged on a first rod and at least two microwave beam receivers arranged on a second rod, the first and second rod running through the plane, at least one of the emitters being arranged in one of the layers and at least one of the receivers being arranged in another layer;

a microwave beam source that can be connected to the emitters and processing means for recording and analysing the microwave beams received by the receivers and the microwave beam emitted by the source.

According to the invention, the first rod and the second rod can be vertical and be spaced from 5 mm to 50 mm apart from one another. The distance between two successive emitters on the first rod can range between 10 mm and 30 mm, and the distance between two successive receivers on the second rod can range between 10 mm and 30 mm. The source can emit a microwave beam whose frequency ranges between 2 and 10 GHz. A receiver can be located at an intermediate height between the height of two adjacent emitters.

The invention also relates to a method using the device described above for determining the position, the composition and the nature of several superposed fluid layers, wherein the following stages are carried out:

a) the source emits a microwave beam;
b) the processing means records the microwave beam emitted by the source;
c) one of the emitters is connected to the source;
d) the processing means records the microwave beam received by each receiver,
e) stages c) and d) are carried out for each emitter; and
f) the processing means analyzes the microwave beams recorded during stages b) and d).

According to an embodiment, stages a) to e) can be carried out with the source emitting a microwave beam of frequency f1, then stages a) to e) can be carried out with the source emitting a microwave beam of frequency f2, frequency f1 being different from frequency f2.

According to another embodiment, stages a) to a) can be carried out with the source emitting a microwave beam of frequency f1, then stages a) to e) can be carried out with the source emitting a microwave beam of frequency f2, then stages a) to e) can be carried out with the source emitting a microwave beam of frequency f3, then stages a) to e) can be carried out with the source emitting a microwave beam of frequency f4, frequencies f1, f2, f3 and f4 being all different.

According to the invention, in stage f), the processing means can record and analyze the intensity variation and the phase variation between the microwave beam emitted by the source and the microwave beam received by a receiver.

The device and the method according to the invention can be used to:

determine the level of the fluids contained in a separating drum in petroleum production;

determine the proportion of oil and of water that constitute the oil/water emulsion contained in a separating drum in petroleum production; and determine the proportion of water present in the oil leaving a separating drum.

The use of microwave beams is less dangerous than gamma rays because the radiated energy is about one thousand times lower.

Furthermore, the microwave detectors permit the nature and the composition of the emulsion to be determined. The nature of the emulsion is known by determining the continuous liquid in which the drops of a second liquid are dispersed, for example: the presence of water drops dispersed in oil, or conversely the dispersion of oil drops in water. The composition gives the proportions of oil and water that constitute the emulsion.

BRIEF DESCRIPTION OF THE DRAWINGS

Other features and advantages of the present invention will be clear from reading the description hereafter, with reference to the accompanying figures wherein.

DETAILED DESCRIPTION

Figure 1:
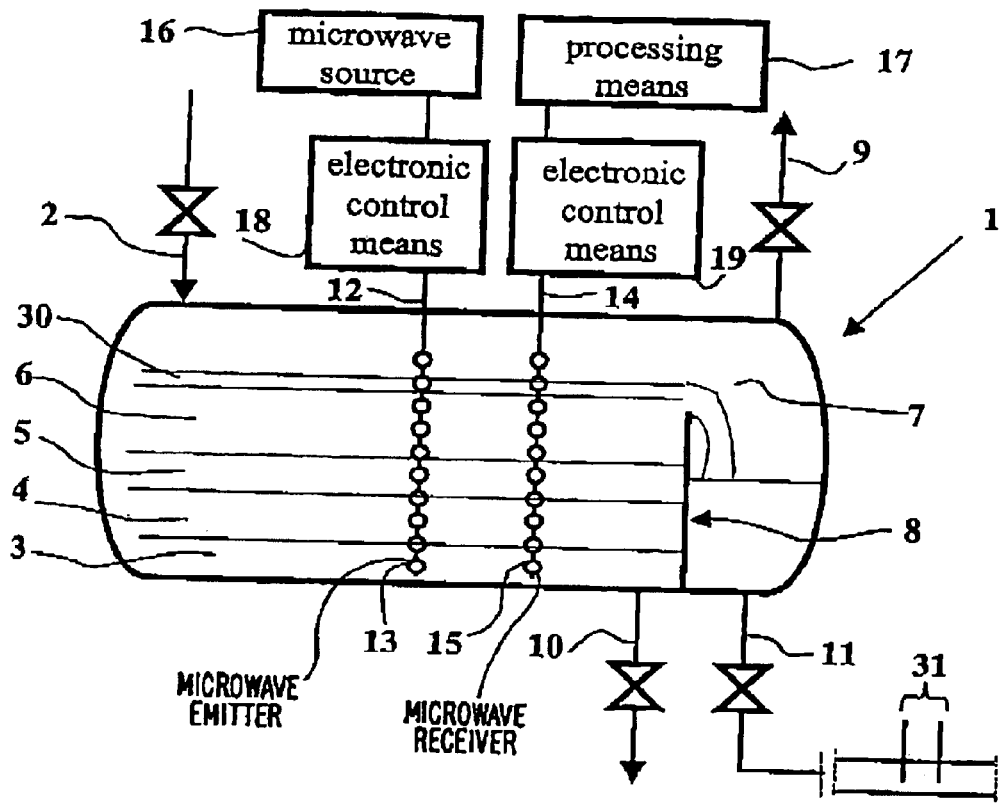
FIG. 1 shows a separating drum provided with microwave detectors.

FIG. 1 shows a separating drum 1. Barrier 8 divides the lower zone of drum 1 into two parts. Upstream from barrier 8, line 2 supplies separating drum 1 with petroleum effluent. The section of line 2 is very small in relation to the section of drum 1, for example ten times smaller. Thus, the petroleum effluent flows at low velocity into drum 1 and it can settle. Under the effect of gravity, the various elements that constitute the petroleum effluent separate and divide in form of layers according to the density of each element. The various layers are superposed. The interfaces which are defined by the boundaries between the layers form horizontal planes. Gas 7 is discharged through line 9 in the upper part of drum 1. Upstream from barrier 8, sand 3 settles at the bottom of drum 1, the water separates from the oil in form of three superposed layers. Water 4 forms a layer above sand 3 and water/oil emulsion layer 5 separates water layer 4 from oil layer 6. An oil foam layer 30 separates oil layer 6 and gas 7. Water 4 is discharged through line 10 upstream from barrier 8. Thus, the oil flows into the part of the separating drum located downstream from barrier 8. Downstream from barrier 8, line 11 allows to discharge the oil from the drum. For the geometry of the separating drum, the positions of the various layers vary notably according to the composition and the flow rate of the effluent flowing in through line 2 and according to the flow rate of the water discharged through line 10.

Drum 1 is provided with a device for detecting the level of water 4, water/oil emulsion 5, oil 6 and oil foam 30 layers. The detection device can be arranged before barrier 8. The detection device has a first rod 12 provided with microwave beam emitters 13 and of a second rod 14 provided with microwave beam receivers 15. The layout of the rods, emitters and receivers is selected so as to limit reflection of the microwave beams on the walls of separating drum 1 and to limit measurement of such reflected microwave beams. Thus, receivers 15 measure the characteristics of the beams coming directly from emitters 13 without taking account of interferences such as the reflected beams. The rods can be metal bars, of square section for example. Rods 12 and 14 run through the interfaces that separate the various layers formed downstream from barrier 8. The rods can be rectilinear, parallel for example. The rectilinear rods can be inclined at 20°, preferably 10° to the vertical. The rods can also be vertical. Rod 12 is close to rod 14 and the distance between the two rods is known. For example, the distance between rods 12 and 14 measured on a horizontal line can range between 5 mm and 50 mm. Emitters 13 and receivers 15 are arranged in such a way that at least one of the emitters is located in a layer of a fluid and at least one of the receivers is located in a layer of another fluid. It is thus possible to know, by analyzing the information picked up by this emitter, that there is an interface between this emitter and this receiver. In addition, emitters 13 and receivers 15 can be arranged in such a way that at least one emitter and one receiver are located in the same layer. It is thus possible to determine, by analyzing the information picked up by this emitter, the composition and possibly the nature of this layer. The layout of emitters 13 and receivers 15 takes into account the possible position variation of the various layers. Emitters 13 can be arranged over the total height of drum 1, at regular intervals for example (thirty emitters 30 mm apart). Receivers 15 can also be arranged over the total height of drum 13 at regular intervals for example (thirty receivers 30 mm apart). A receiver 15 can be arranged at a height located between the heights of two emitters 13 which are adjacent on rod 12, for example in the middle of these two emitters. This layout increases the amount of information measured by the detection device, and therefore to increase the accuracy in relation to a layout where each receiver 15 is arranged at the same height as one of emitters 13. A receiver 15 can correspond to each emitter 13. Emitters 13 and receivers 15 can also be positioned in such a way that at least one emitter is arranged in each layer and/or a receiver is arranged in each layer and/or at least one emitter and one receiver are arranged in each layer.

A source 16 generates a microwave beam that is transmitted to emitters 13. The microwave beam can be a beam of electromagnetic energy or electromagnetic field of frequency ranging between 1 and 100 GHz, preferably between 2 and 10 GHz this beam generated by the source is characterized by an intensity value and a phase. Electronic control means 18 allow connection of source 16 to one or more emitters 13. The microwave beam is emitted by emitters 13 to radiate the petroleum effluent. After travelling the distance between the two rods, the beam is picked up by receivers 15. As it runs through one of the fluids that constitute the petroleum effluent, the intensity and the phase of the beam are modified. The beam received by receivers 15 is sent to data processing means 17. Electronic control means 19 allow connection of one or more receivers 15 to data processing means 17. The data processing means 17 records and compares the characteristics (intensity and phase) of the beam emitted by one of emitters 13 and the characteristics (intensity and phase) of the beam received by a receiver 15. It is thus possible to know, on the one hand, the attenuation of the microwave beam, that is the ratio of the intensity of the beam emitted by an emitter 13 to the intensity of the beam received by a receiver 15, and on the other hand the phase shift of the microwave beam, that is the difference between the phase of the beam emitted by an emitter 13 and the phase of the beam received by a receiver 15. Analysis of these comparisons allows determination of the nature and the composition of the fluid that separates the emitter from the receiver.

Figure 2:
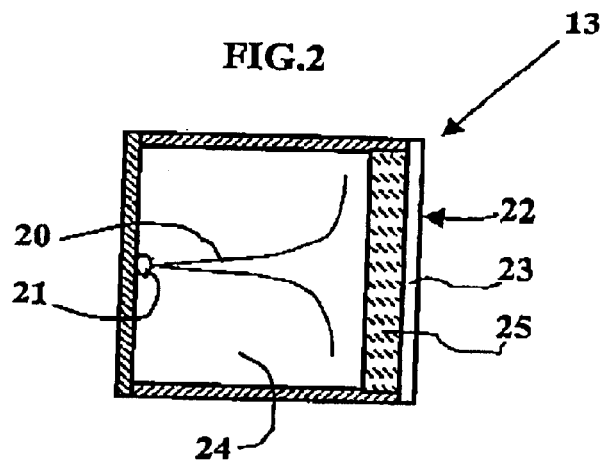
FIG. 2 diagrammatically shows in detail a microwave emitter.

Emitter 13 shown in FIG. 2 is substantially cubic. It comprises an antenna 20 with two branches moulded in a resin 24, an epoxy resin for example. Five sides of the cube are coated with a material impervious to microwave beams with only side 22 being permeable to microwave beams. Side 22 of the emitter is coated with a material 25 having a low microwave beam attenuation coefficient, a ceramic type material for example. The function of this material is to adjust the impedance of emitter 13 to the nature of the fluid in contact therewith. Furthermore, ceramic material 25 is protected from chemical attack by the petroleum effluent by means of a layer 23 made of polyvinylidene fluoride (PVDF) for example. The two branches of antenna 20 extend in the cube before side 22 in contact with the petroleum effluent.

The antenna can have the shape of a wire or of a metal strap, copper for example. Electronic control means 18 allow establishing a contact between connection 21 and microwave source 18.

Owing to the plane geometry of emitter 13, the microwave beams are emitted through side 22. The microwave beams radiate in the total volume surrounding emitter 13 with no preferred direction. There is no polarization of the microwave beam, due for example to a crossed position of two emitters. Polarization provides no pertinent information for data analysis. Thus, the emission of microwave beams according to the invention affords the advantage of being simple.

Receivers 15 are physically identical to emitters 13. Emitters 13 and receivers 15 are identical electromagnetic antennas and their roles can be reversed.

The measuring method can comprise the following stages:
1) source 16 generates a microwave beam of frequency f1;
2) part of the microwave beam is transmitted to data processing means 17; this part of the beam, referred to as reference beam, has the characteristics (intensity and phase) of the beam emitted by an emitter 13 in stage 3);
3) electronic control means 18 bring one of emitters 13 into contact with source 16; emitter 13 emits the microwave beam that is propagated through the fluid contained between rods 12 and 14 up to receivers 15;
4) electronic control means 19 bring each receiver 15 into contact with data processing means 17; thus, the data processing means 17 records the beam received by each receiver 15; for example, for a rod 14 comprising thirty receivers 15, data processing means 17 records thirty measurements; analysis of the data picked up by each receiver 15 allows determination of the receivers which are located in the same layer as the active emitter and the receivers which are located in the other layers; it is thus possible to know the position of the interfaces which delimit the layer in which active emitter 13 is positioned; analysis of the data picked up by receivers 15 arranged in the same layer as active emitter 13 allows determination of the composition and possibly the nature of this layer;
5) data processing means 17 performs, on the one hand, a comparison between the intensity of the reference beam and the intensity of the beam received by one of receivers 15 (in the description hereafter, the intensity variation is referred to as wave attenuation) and, on the other hand, the receivers measure the phase shift between the reference beam and the beam received by one of receivers 15;
6) stages 3, 4 and 5 are repeated for each emitter 13; emitters 13 are thus successively connected to the source so as to successively emit a microwave beam. If rod 12 comprises thirty emitters 13 and rod 14 comprises thirty receivers 15, data processing means 17 carries out nine hundred measurements; thus, by positioning emitters 13 in such a way that there is at least one emitter in each layer. It is possible to determine, for each layer, the position of the interfaces that delimit each layer, as well as the composition and possibly the nature of each layer; and
7) stages 1 to 6 are repeated for several different values of frequency f1; for example, stages 1 to 6 can be carried out for the four successive values of f1:2 GHz, 3 GHz, 4 GHz and 6 GHz.

Without departing from the scope of the invention, stages 1 to 7 can be carried out in a different order.

Exploitation of the attenuation and phase shift values measured by data processing means 17 in stage 4) allows determination of the position of the interfaces. In general: gas/oil or oil/water, and in particular detection of the intermediate layers between the gas and the oil, that is a foam layer, and between the oil and the water, that is the emulsion layer.

The attenuation of a wave, as well as its phase shift, depends on parameters intrinsic to the fluids crossed, such as the salinity of the water and the permittivity of the fluids (the permittivity of a fluid varying as a function of the frequency of the wave passing through the fluid). For example, at a frequency of 20 GHz, the permittivity is approximately 2 when the wave runs through the fluid containing oil. The permittivity increases when the wave runs through oil containing more and more water, until it reaches a value of the order of 80 when the wave runs through water only.

The nature of the fluid contained between an emitter 13 and a receiver 15 whose positions are known is determined from the transmission of a wave of known frequency f1 between the emitter and the receiver and from the attenuation and phase shift measurements. This analysis being repeated for each emitter 13 and receiver 15, it is possible to determine with precision the position of the interfaces between the various fluid layers present in the separating drum.

Selection of the frequency of the microwave beam emitted by the source can also be optimized. In fact, the permittivity being a function of the frequency of the wave running through the fluid, it is possible to carry out a series of measurements at a frequency for which the attenuation and the phase shift through the water are high in relation to the oil, then another series of measurements at a frequency for which the attenuation and the phase shift through the oil are high in relation to the gas.

The measurements performed by data processing means 17 also allows determination of the nature and the composition of the emulsion layer and the composition of the foam layer.

The permittivity value of the emulsion depends on the nature of the emulsion. The permittivity of the emulsion can therefore be calculated to know the nature of the emulsion, from measurements of the attenuation and of the phase shift of a wave of frequency f1 running through an emulsion layer.

From a multifrequency calibration, the oil and water composition of the emulsion and the gas composition of the foam are determined by means of a specific processing of all of the data resulting from the attenuation and phase shift measurements. This specific processing is based on a "signal processing" type data exploitation and on a statistical analysis.

The present invention allows determination of the level of the various fluids present in a separating drum used for production of a petroleum effluent. This information allows controlling the effluent inflow rate so as to maintain the interface between the emulsion and the oil below the barrier of the separating drum. The loss of oil in water or the loss of water in oil can thus be minimized.

The device according to the present invention can also be installed at the outlet of a separating drum in the vicinity of the oil discharge line. In FIG. 1, the device according to the invention bearing reference number 31 is installed on line 11. The two rods comprising the emitters and the receivers are substantially perpendicular to the axis of line 11. In this case, the amount of water present in the oil leaving the separating drum can be determined.

The present invention also allows knowing the nature and the composition of the emulsified oil/water layer separating the oil layer from the water layer and of the oil form/gas layer separating the oil layer from the gas layer. This information allows optimizing the operating conditions of the separating drum (stirring, presence of a pump, valves, and parameters such as the pressure, the temperature and the physico-chemical composition of the oil and of the water), to control the introduction of stabilizing and demulsifying chemical agents in the petroleum effluent downstream from the separating drum and/or to actuate flow stabilization devices in the separating drum.

What is claimed is:

1. A device for determining information about superposed fluid layers, comprising:

a separating drum containing at least two fluids arranged in superposed layers, and an interface formed by a boundary between two of the superposed layers being a horizontal plane, the drum comprising at least two microwave emitters arranged longitudinally along a first device and at least two microwave receivers arranged longitudinally along a second device, the first and second devices running through the horizontal plane, at least one of the microwave emitters being arranged in one of the superposed layers and at least one of the microwave receivers being arranged in another layer of the superposed layers;

a microwave source which is selectively connectable to the at least two microwave emitters to couple microwaves thereto; and a processor for recording and analyzing microwaves received by receivers and microwaves provided by the microwave source to determine the information about the superposed fluid layers.

2. A device as claimed in claim 1, wherein the first and second devices are vertical and spaced from 5 mm to 50 nm apart from one another.

3. A device as claimed in claim 1, wherein:

a distance between two successive emitters on the first device ranges between 10 mm and 30 mm, and a distance between two successive receivers on the second device ranges between 10 mm and 30 mm.

4. A device as claimed in claim 1, wherein:

a microwave receiver is located at an intermediate height between heights of two adjacent microwave emitters.

5. A device as claimed in claim 1, wherein:

the microwave source emits a microwave beam whose frequency ranges between 2 and 10 GHz.

6. A method using the device as claimed in claim 1 for determining information about the superposed layers comprising:

a) the microwave source emits a microwave beam;

b) the processor records the microwave beam emitted by the microwave source;

c) one of the emitters is connected to the microwave source;

d) the processor records the microwave beam received by each receiver;

e) steps c) and d) are carried out for each microwave emitter; and f) the processor analyzes the microwave beams recorded during steps b) and d).

7. A method as claimed in claim 6, wherein steps a) to e) are carried out with the microwave source emitting a microwave beam of frequency f1 then steps a) to e) are carried out with the microwave source emitting a microwave beam of frequency f2, frequency f1 being different from frequency f2.

8. A method as claimed in claim 6, wherein steps a) to e) are carried out with the microwave source emitting a microwave beam of frequency f1, then steps a) to e) are carried out with the microwave source emitting a microwave beam of frequency f2, then steps a) to e) are carried out with the microwave source emitting a microwave beam of frequency f3, then steps a) to e) are carried out with the microwave source emitting a microwave beam of frequency f4, frequencies f1, f2, f3 and f4 being all different.

9. A method as claimed in claim 6, wherein in step f), the processor records and analyzes an intensity variation and a phase variation between the microwave beam emitted by the microwave source and the microwave beam received by a receiver.

10. A use of the device as claimed in claim 1 and of the method as claimed in claim 2 for determining a level of the fluids contained in the separating drum in petroleum production.

11. A use of the device as claimed in claim 1 and of the method as claimed in claim 6 for determining a proportion of oil and of water that constitute an oil/water emulsion contained in the separating drum in petroleum production.

12. A use of the device as claimed in claim 1 and of the method as claimed in claim 6 determining a proportion of water present in oil leaving the separating drum.

* * * * *